United States Patent [19]
Okamoto et al.

[11] Patent Number: 5,427,909
[45] Date of Patent: Jun. 27, 1995

[54] OLIGONUCLEOTIDES AND DETERMINATION SYSTEM OF HCV GENOTYPES

[75] Inventors: Hiroaki Okamoto, Tochigi; Tetsuo Nakamura, Tokyo, both of Japan

[73] Assignee: Immuno Japan Inc., Tokyo, Japan

[21] Appl. No.: 940,242

[22] Filed: Sep. 8, 1992

[30] Foreign Application Priority Data

Sep. 9, 1991 [JP] Japan ................... 3-307296
Feb. 28, 1992 [JP] Japan ................... 4-093960

[51] Int. Cl.[6] ............... C12Q 1/68; C12Q 1/70; C12P 19/34; C07H 21/04
[52] U.S. Cl. .......................... 435/54; 435/6; 435/91.1; 435/91.2; 536/24.33
[58] Field of Search ............ 435/91, 5, 91.1, 91.2; 536/24.33; 935/18, 78

[56] References Cited

FOREIGN PATENT DOCUMENTS

| | | |
|---|---|---|
| 0388232 | 9/1990 | European Pat. Off. . |
| 0485209 | 5/1992 | European Pat. Off. . |
| 2654113 | 5/1991 | France . |
| 92/02642 | 2/1992 | WIPO . |
| 92/19743 | 11/1992 | WIPO . |

OTHER PUBLICATIONS

Takamizawa et al. J. of Virol. 65: 1105–1113 (1991).
Inchanspe et al. P.N.A.S. 88: 10292–10296 (1991).
Okamoto et al. J. Gener. Virol. 72: 2697–2704 (1991).
Okamoto et al. Nuc. Acids Res. 20: 6410 (1992).
Kwok et al. in "PCR Technology: Principles and Applications for DNA Amplification" pp. 235–242, ed. H. Erlich (1990).
Sequence Search Printout. pp. 1–153 (1993).
Nakao, T., et al "Typing of hepatitis C virus genomes by restriction fragment length polymorphism", J. General Virology (Sep. 1991), vol. 72, pp. 2105–2112.
Okamoto, H., et al., "Typing hepatitis C by polymerase chain reaction with type-specific primers: application to clincal surveys and tracing infectious sources", J. General Virology (Mar. 1992), vol. 73, pp. 673–679.
Yoshioka, K., et al., "Detection of hepatitis C virus by polymerase chain reaction and response to interferon-αtherapy: relationship to genotypes of hepatitis C virus", HJepatology (Aug. 1992), vol. 16, pp. 293–299.

Primary Examiner—Margaret Parr
Assistant Examiner—Paul B. Tran
Attorney, Agent, or Firm—Beveridge, DeGrandi, Weilacher & Young

[57] ABSTRACT

Hepatitis C virus oligonucleotides and a system to determine hepatitis C virus genotypes with polymerase chain reaction utilizing those oligonucleotides as primers.

18 Claims, 5 Drawing Sheets

FIG. 6

| TYPE | CLONE No. | #256(S) 139–158 CGCGCGACTAGGAAGACTTC | #296(AS) 177–196 AGGTAGACGTCAGCCTATCC |
|---|---|---|---|
| I | 1 | ——————G—————— | ———————————————— |
|  | 2 | ——————G—————— | ———————————————— |
|  | 3 | ——————G—————— | ———————————————— |
|  | 4 | ——————G—————— | ———————————————— |
| II | 5 | ———————————————— | T—A—G—A—A—— |
|  | 6 | ————————G————— | T—A—G—A—A—— |
|  | 7 | ———————————————— | T—A—G—A—A—— |
|  | 8 | ———————————————— | T—A—G—A—A—— |
|  | 9 | ———————————————— | T—C—G—A—A—— |
|  | 10 | ———————————————— | T—A—G—A—A—— |
|  | 11 | ———————————————— | T—A—G—A—A—— |
|  | 12 | ———————————————— | T—A—G—A—A—— |
|  | 13 | ———————————————— | T—A—G—A—A—— |
|  | 14 | ———————————————— | T—G—G—A—A——T— |
|  | 15 | ———————————————— | T—A—G—A—A—— |
|  | 16 | ———————————————— | T—A—G—A—A—— |
|  | 17 | ———————————————— | T—A—G—A—A—— |
|  | 18 | ———————————————— | T—G—G—A—A—— |
|  | 19 | ———————————————— | T—A—G—A—A—— |
|  | 20 | ———————————————— | T—A—G—A—A—— |
|  | 21 | ———————————————— | T—A—G—A—A—— |
|  | 22 | ———————————————— | T—A—G—A—A—— |
|  | 23 | ———————————————— | T—A—G—A—A—— |
|  | 24 | ———————————————— | T—A—G———A—— |
| III | 25 | ——————C-C——————— | T—G—G—C———C— |
|  | 26 | ——————A——————— | T—A—G—C———C— |
|  | 27 | ——————A——————— | T—A—G—C———C— |
|  | 28 | ——————A——————— | C—G—G—C———C— |
|  | 29 | ——————G——————— | T—G—G—C———C— |
|  | 30 | ——————A——A——— | T—G—G—C———C— |
|  | 31 | ——————A——————— | T—G—G—C———C— |
|  | 32 | ——————A——————— | T—G—G—C———C— |
|  | 33 | ——————A——————— | T—G—G—C———C— |
|  | 34 | ——————A——————— | T—AG—G—C———C— |
| IV | 35 | ——————A——————— | T—G———C———C— |
|  | 36 | ——————G——————— | T—G———C———C— |
|  | 37 | ——————A——————— | T—AC———C———C— |
|  | 38 | ——————A——————— | T—G———C———C— |
|  | 39 | ——————A——————— | T—G—G—C———C— |

SEQUENCE LISTING ( 1 ) GENERAL INFORMATION:

( i i i ) NUMBER OF SEQUENCES: 99

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

YRCCTTGGGG ATAGGCTGAC                                              20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GARCCA W CCT GCCCAYCCYA                                      20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CCAARAGGGA CGGGARCCTC                                           20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

RCCYTCGTTT CCRTACAGRG                                           20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

AGRAARRCTT CSGAGCGRTC                                           20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single (D) TOPOLOGY: linear (xi) SEQUENCE DESCRIPTION: SEQ ID NO:6:

TAGATTGGGT GTGCGCGCGA                                           20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:7:

CGCGCGMCNA GGAARRCTTC                                           20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

AYGTACCCCA YGAGRTCGGC                                           20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

GGATAGGCTG ACGTCTACCT                                           20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:10:

AACACTACTC GGCTAGCAGT                                           20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:11:

CTGTGAGGAA CTACTGTCTT                                           20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:12:

TTCACGCAGA AAGCGTCTAG                                                            20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GTTGATCCAA GAAAGGACCC                                                            20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

AGGTTCCCTG TTGCATAATT                                                            20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

TGCCTTGGGG ATAGGCTGAC                                                            20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GAGCCATCCT GCCCACCCCA                                                            20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CCAAGAGGGA CGGGAACCTC                                                            20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

ACCCTCGTTT CCGTACAGAG                                                            20

( 2 ) INFORMATION FOR SEQ ID NO:19:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:19:

AGGAAGACTT CCGAGCGGTC 20

( 2 ) INFORMATION FOR SEQ ID NO:20:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:20:

CGCGCGACTA GGAAGACTTC 20

( 2 ) INFORMATION FOR SEQ ID NO:21:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:21:

ATGTACCCCA TGAGGTCGGC 20

( 2 ) INFORMATION FOR SEQ ID NO:22:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:22:

AGGAAGGCTT CCGAGCGGTC 20

( 2 ) INFORMATION FOR SEQ ID NO:23:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:23:

AGGAAGACTT CCGAGCGATC 20

( 2 ) INFORMATION FOR SEQ ID NO:24:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:24:

AGGAAGACTT CGGAGCGGTC 20

( 2 ) INFORMATION FOR SEQ ID NO:25:

( i ) SEQUENCE CHARACTERISTICS:
      ( A ) LENGTH: 20 base pairs
      ( B ) TYPE: nucleic acid (C) STRANDEDNESS: single
(D) TOPOLOGY: linear (xi) SEQUENCE DESCRIPTION: SEQ ID NO:25:

AGGAAAACTT CGGAGCGGTC                   20

(2) INFORMATION FOR SEQ ID NO:26:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:26:

AGGAAGACTT CCGAGCGATC                   20

(2) INFORMATION FOR SEQ ID NO:27:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:27:

GTCAGCCTAT CCCCAAGGTG                   20

(2) INFORMATION FOR SEQ ID NO:28:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:28:

GACAACCTAT CCCCAAGGCT                   20

(2) INFORMATION FOR SEQ ID NO:29:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:29:

GACAACCTAT CCTCAAGGCT                   20

(2) INFORMATION FOR SEQ ID NO:30:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:30:

GACAACCTAT TCCCAAGGTT                   20

(2) INFORMATION FOR SEQ ID NO:31:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:31:

GCCAGCCCAT CCCCAAAGAT 20

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

GCCAGCCCAT CCCTAAGGAT 20

( 2 ) INFORMATION FOR SEQ ID NO:33:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

GCCAGCCCAT CCCCAGAGAT 20

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

GCCAGCCCAT CCCGAAAGAT 20

( 2 ) INFORMATION FOR SEQ ID NO:35:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

GCGGGTGGGC GGGATGCCTC 20

( 2 ) INFORMATION FOR SEQ ID NO:36:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

TGGGATGGGC AGGATGCCTC 20

( 2 ) INFORMATION FOR SEQ ID NO:37:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

TGGGGTGGGC AGGTTGCCTC 20

( 2 ) INFORMATION FOR SEQ ID NO:38:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

TGGGGTGGGC AGGATGCTTC         20

( 2 ) INFORMATION FOR SEQ ID NO:39:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

TAGGGTGGGC AGGATGCCTC         20

( 2 ) INFORMATION FOR SEQ ID NO:40:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

TCGGTTGGGC AGGATGCCTC         20

( 2 ) INFORMATION FOR SEQ ID NO:41:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

TCGGCTGGGC AGGGTGCCTC         20

( 2 ) INFORMATION FOR SEQ ID NO:42:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

TCGGCTGGGC AGGATGCCTC         20

( 2 ) INFORMATION FOR SEQ ID NO:43:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

TCGGATGGGC AGGATGCCTC         20

( 2 ) INFORMATION FOR SEQ ID NO:44:

( i ) SEQUENCE CHARACTERISTICS:
        ( A ) LENGTH: 20 base pairs (B) TYPE: nucleic acid
        (C) STRANDEDNESS: single
        (D) TOPOLOGY: linear (xi) SEQUENCE DESCRIPTION: SEQ ID NO:44:

TCGGCTGGGC AGGATGCCTT                         20

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:45:

TCGGCTGGGC AGGTTGCCTC                         20

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:46:

GCGGCTGGGC AGGTTGCCTC                         20

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:47:

GCGGCTGGGC GGGTTGCCTC                         20

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:48:

GTGGCTCTCG GCCTAGTTGG                         20

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:49:

GTGGCTCTCG GCCTAGCTGG                         20

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear ( x i ) SEQUENCE DESCRIPTION: SEQ ID NO:50:

GCGGCTCCCG GCCTAGTTGG 20

( 2 ) INFORMATION FOR SEQ ID NO:51:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

GCGGCTCTCG GCCTAGTTGG 20

( 2 ) INFORMATION FOR SEQ ID NO:52:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

GTGGTTCTCG GCCTAGTTGG 20

( 2 ) INFORMATION FOR SEQ ID NO:53:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

GCGGCTCTCG GCCCAGTTGG 20

( 2 ) INFORMATION FOR SEQ ID NO:54:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

GTGGCTCTCG GCCTAGTTGG 20

( 2 ) INFORMATION FOR SEQ ID NO:55:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

GAGGCTCTCG GCCTAGTTGG 20

( 2 ) INFORMATION FOR SEQ ID NO:56:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

GTGGCTCTCG GCCTAATTGG 20

( 2 ) INFORMATION FOR SEQ ID NO:57:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

GCGGCTCTCG ACCTAGTTGG                                               20

( 2 ) INFORMATION FOR SEQ ID NO:58:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

GTGGCTCCCG GCCTAGTTGG                                               20

( 2 ) INFORMATION FOR SEQ ID NO:59:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

GCGGCTCTCG GCCTAATTGG                                               20

( 2 ) INFORMATION FOR SEQ ID NO:60:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

GAGGCTCCCG TCCCTCTTGG                                               20

( 2 ) INFORMATION FOR SEQ ID NO:61:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

GAGGTTCCCG TCCCTTTTGG                                               20

( 2 ) INFORMATION FOR SEQ ID NO:62:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

GCGGGTCTCG TCCTACTTGG                                               20

( 2 ) INFORMATION FOR SEQ ID NO:63:

( i ) SEQUENCE CHARACTERISTICS:

(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:63:

CCCTCTATGG CAATGAGGGC  20

(2) INFORMATION FOR SEQ ID NO:64:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:64:

CCCTCTATGG CAATGAGGGT  20

(2) INFORMATION FOR SEQ ID NO:65:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:65:

CCCTCTACGG CAATGAGGGC  20

(2) INFORMATION FOR SEQ ID NO:66:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:66:

CCCTCTATGG CAACGAGGGC  20

(2) INFORMATION FOR SEQ ID NO:67:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:67:

CCCTCTATGG CAACAAGGGC  20

(2) INFORMATION FOR SEQ ID NO:68:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:68:

CCCTCTACGG CAACGAGGGC  20

(2) INFORMATION FOR SEQ ID NO:69:

(i) SEQUENCE CHARACTERISTICS:
(A) LENGTH: 20 base pairs
(B) TYPE: nucleic acid
(C) STRANDEDNESS: single
(D) TOPOLOGY: linear ( x i ) SEQUENCE DESCRIPTION: SEQ ID NO:69:

CCCTATATGG GAATGAGGGG 20

( 2 ) INFORMATION FOR SEQ ID NO:70:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

CCCTATATGG GAATGAGGGA 20

( 2 ) INFORMATION FOR SEQ ID NO:71:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

CCCTATACGG GAATGAGGGA 20

( 2 ) INFORMATION FOR SEQ ID NO:72:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

CTCTATATGG GAATGAGGGA 20

( 2 ) INFORMATION FOR SEQ ID NO:73:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

CCCTATACGG GAATGAGGGG 20

( 2 ) INFORMATION FOR SEQ ID NO:74:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:74:

CCCTGTATGG GAACGAGGGA 20

( 2 ) INFORMATION FOR SEQ ID NO:75:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

CCCTGTATGG GAATGAGGGA 20

( 2 ) INFORMATION FOR SEQ ID NO:76:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:76:

CTCTGTATGG AAACGAGGGC       20

( 2 ) INFORMATION FOR SEQ ID NO:77:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:77:

CTCTGTACGG AAACGAAGGC       20

( 2 ) INFORMATION FOR SEQ ID NO:78:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

CCCTGTACGG AAACGAGGGT       20

( 2 ) INFORMATION FOR SEQ ID NO:79:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:79:

CTCTGTATGG AAACGAGGGT       20

( 2 ) INFORMATION FOR SEQ ID NO:80:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:80:

GCCGACCTCG TGGGGTACAT       20

( 2 ) INFORMATION FOR SEQ ID NO:81:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:81:

GCCGATCTCA TGGGGTACAT       20

( 2 ) INFORMATION FOR SEQ ID NO:82:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:82:

GCCGACCTCG TGGGGTACGT                                                                 20

( 2 ) INFORMATION FOR SEQ ID NO:83:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

CGCGCGACGA GGAAGACTTC                                                                 20

( 2 ) INFORMATION FOR SEQ ID NO:84:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

CGCGCGACTA GGAAGGCTTC                                                                 20

( 2 ) INFORMATION FOR SEQ ID NO:85:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

CGCGCGCCCA GGAAGACTTC                                                                 20

( 2 ) INFORMATION FOR SEQ ID NO:86:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

CGCGCGACAA GGAAGACTTC                                                                 20

( 2 ) INFORMATION FOR SEQ ID NO:87:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:87:

CGCGCGACGA GGAAGACTTC                                                                 20

( 2 ) INFORMATION FOR SEQ ID NO:88:

( i ) SEQUENCE CHARACTERISTICS:
        ( A ) LENGTH: 20 base pairs
        ( B ) TYPE: nucleic acid
        ( C ) STRANDEDNESS: single -continued (D) TOPOLOGY: linear (xi) SEQUENCE DESCRIPTION: SEQ ID NO:88:

CGCGCGACAA GGAAAACTTC                                                    20

(2) INFORMATION FOR SEQ ID NO:89:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:89:

TGGAAGGCGA CAACCTATCC                                                    20

(2) INFORMATION FOR SEQ ID NO:90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:90:

TGGCAGGCGA CAACCTATCC                                                    20

(2) INFORMATION FOR SEQ ID NO:91:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:91:

TGGGAGGCGA CAACCTATTC                                                    20

(2) INFORMATION FOR SEQ ID NO:92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:92:

TGGGAGGCGA CAACCTATCC                                                    20

(2) INFORMATION FOR SEQ ID NO:93:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:93:

TGGAAGGCGT CAACCTATCC                                                    20

(2) INFORMATION FOR SEQ ID NO:94:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:94:

TGGGAGGCGC CAGCCCATCC                                              20

( 2 ) INFORMATION FOR SEQ ID NO:95:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:95:

CGGGAGGCGC CAGCCCATCC                                              20

( 2 ) INFORMATION FOR SEQ ID NO:96:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:96:

TGAGAGGCGC CAGCCCATCC                                              20

( 2 ) INFORMATION FOR SEQ ID NO:97:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:97:

TGGGAGACGC CAGCCCATCC                                              20

( 2 ) INFORMATION FOR SEQ ID NO:98:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:98:

TGGACGACGC CAGCCCATCC                                              20

( 2 ) INFORMATION FOR SEQ ID NO:99:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:99:

TGGGAGGCGC CAGCCCATCC                                              20

OLIGONUCLEOTIDES AND DETERMINATION SYSTEM OF HCV GENOTYPES

BACKGROUND OF THE INVENTION

The present invention concerns hepatitis C virus (hereinafter called HCV) oligonucleotides and a system to determine HCV genotypes with polymerase chain reaction (PCR) utilizing those oligonucleotides as primers.

Viral hepatitis of which DNA and RNA of the causative viruses have been elucidated, and their diagnosis and even prevention in some cases have been established, are hepatitis A and hepatitis B. The general name NANB (non-A, non-B) hepatitis was given to the other forms of viral hepatitis.

Post-transfusion hepatitis was remarkably reduced after introduction of diagnostic systems for screening hepatitis B virus in transfusion bloods. However, there are still an estimated 280,000 annual cases of post-transfusion hepatitis caused by NANB hepatitis virus in Japan.

NANB hepatitis viruses were recently named C, D and E according to their types, and scientists started a world wide effort to conduct research for the causative viruses.

In 1988, Chiron Corp. claimed that it had succeeded in cloning RNA virus genome, which it termed hepatitis C virus (HCV), as the causative agent of NANB hepatitis and reported on its nucleotide sequence (British Patent 2,212,511 which is the equivalent of European Patent Application 0,318,216). HCV (c100-3) antibody detection systems based on the sequence are now being introduced for screening of transfusion bloods and for diagnosis of patients in Japan and in many other countries.

The detection systems for the c100-3 antibody have proven their partial association with NANB hepatitis; however, they capture only about 70% of carriers and chronic hepatitis patients, or they fail to detect the antibody in acute phase infection, thus leaving problems yet to be solved even after development of the c100-3 antibody by Chiron Corp.

The genome structure of HCV, or NANB hepatitis having relation to c100-3 antibody, has single stranded RNA which suggests some relationship to Flaviviruses and Pestiviruses. From the comparison of those genome structures, regions coding core protein (C), envelope protein (E) and non-structure protein (NS) were found in HCV. c100-3 antibody detected by Chiron's ELISA kit is thought to recognize a part of the border region of NS3/NS4.

The course of NANB hepatitis is troublesome and many cases of horizontal transmission are considered to become carriers and then to develop chronic hepatitis. In addition, most patients with chronic hepatitis develop liver cirrhosis, then hepatocellular carcinoma. It is therefore very imperative to isolate the virus itself and to develop effective diagnostic reagents enabling earlier diagnosis.

The presence of a number of NANB hepatitis which can not be diagnosed by Chiron's HCV (c100-3) antibody detection kits suggests the importance of detection of antibody to core protein instead of antibody to non-structural protein. From that view point, the genome of the core region and the protein coded for by this region have been studied world wide.

From the two-by-two comparison of nucleotide sequences of various HCV isolates, homologies for the core region, which is rather conservative, were found to be less than 90% in some cases. In addition, more variability was found in the envelope region (which is thought to be important for development of vaccine); less than 60% homology was found between some isolates. The sequence diversity between strains reflects the features of HCV as RNA virus.

A rapid and simple method of classifying of HCV genomes into groups, therefore, would be very useful for diagnosis, therapy and prevention of NANB hepatitis.

Determination of HCV genotypes could be useful in the following medical and social applications:

(1) identification of infectious sources in vertical (mother-to-baby) transmission and horizontal transmission;

(2) clarification of genotype-specific features in the course, condition and prediction of recuperation of NANB liver diseases and making a guide of therapy therefore;

(3) increasing the detection sensitivity of HCV by nucleic acid detection system or antibody detection system based on the study of diversity in nucleotide or amino acid sequences among HCV isolates of distinct genotypes;

(4) production of type-specific immunoglobulin (IgG) and vaccine based on the study of type-specific conservative regions in the envelope gene of various genotypes; and (5) rapid and effective prevention by selecting an appropriate IgG or vaccine for each genotype.

The inventors have obtained various HCV-RNAs from sera of humans and chimpanzees, and cloned cDNAs of HCV genomes in non-coding regions and coding regions for core and envelope proteins, followed by determination of nucleotide sequences (Japanese Patent Applications 196175/91, 287402/91 and 360441/91), and sought to find a method to determine HCV genotypes and oligonucleotide primers to be used in said method, which would be useful in diagnosis, therapy, prevention, identification of infectious source, and epidemiological study on HCV. As a result, variation of nucleotide sequence characteristics in some groups in the core region, which was thought to be rather conservative, was found, and much more variation was found in the envelope region.

SUMMARY OF THE INVENTION

It has been found as a result of study of a great number of nucleotide sequences of HCV isolates that HCVs could be divided into four genotypes through the nucleotide sequence of the putative C gene and based on the homology of nucleotides. Based on this finding, universal oligonucleotides and type-specific oligonucleotides were identified and synthesized.

In accordance with one aspect of the invention, there is provided universal oligonucleotides #104 (sequence list 5), #186 (sequence list 8), and #256 (sequence list 7) and type-specific oligonucleotides #132 (sequence list 1), #133 (sequence list 2), #134 (sequence list 3), #135 (sequence list 4) and #296 (sequence list 5).

A further feature of the invention resides in a method of determining HCV genotypes by polymerase chain reaction (PCR) amplification of cDNA using one or more of said oligonucleotide as primers. The method of determining HCV genotypes could be carried out by measuring lengths of amplification products obtained by PCR described above.

Thus, in accordance with a further aspect of the invention, there is provided a method of determining HCV genotypes. The method involves two stage PCR, wherein the second stage PCR comprises utilizing one or more of oligonucleotides #132 (sequence list 1), #133 (sequence list 2), #134 (sequence list 3), #135 (sequence list 4) and #296 (sequence list 5) as antisense primer and utilizing one or more of oligonucleotides #104 (sequence list 5), #23 (sequence list 6) and #256 (sequence list 7) as sense primer. The method further involves first stage PCR utilizing one or both of oligonucleotides #23 (sequence list 6) and #256 (sequence list 7) as sense primer and #186 (sequence list 8) as antisense primer.

The method to determine genotypes can be used in a method of predicting response of a patient with type C hepatitis to drug therapy.

For primer #104, Clone (SEQ ID NO) is as follows: 5 (SEQ ID NO:22), 18 (SEQ ID NO:23), 25 (SEQ ID NO:24), 30 (SEQ ID NO:26). For primer #132 (sequence list 1), Clone (SEQ ID NO) is as follows: 1 (SEQ ID NO:27), 5 (SEQ ID NO:28), 11 (SEQ ID NO:29), 14 (SEQ ID NO:30), 25 (SEQ ID NO:31), 27 (SEQ ID NO:32), 34 (SEQ ID NO:33), 35 (SEQ ID NO:34). For primer #133, Clone (SEQ ID NO) is as follows: 1 (SEQ ID NO:35), 7 (SEQ ID NO:36), 13 (SEQ ID NO:37), 14 (SEQ ID NO:38), 16 (SEQ ID NO:39), 25 (SEQ ID NO:40), 26 (SEQ ID NO:41), 27 (SEQ ID NO:42), 30 (SEQ ID NO:43), 32 (SEQ ID NO:44), 33 (SEQ ID NO:45), 35 (SEQ ID NO:46), 37 (SEQ ID NO:47). For primer #134, Clone (SEQ ID NO) is as follows: 1 (SEQ ID NO:48), 2 (SEQ ID NO:49), 5 (SEQ ID NO:50), 6 (SEQ ID NO:51), 7 (SEQ ID NO:52), 9 (SEQ ID NO:53), 10 (SEQ ID NO:54), 11 (SEQ ID NO:55), 14 (SEQ ID NO:56), 17 (SEQ ID NO:57), 19 (SEQ ID NO:58), 24 (SEQ ID NO:59), 29 (SEQ ID NO:60), 32 (SEQ ID NO:61), 35 (SEQ ID NO:62). For primer #135, Clone (SEQ ID NO) is as follows: 1 (SEQ ID NO:63), 4 (SEQ ID NO:64), 9 (SEQ ID NO:65), 12 (SEQ ID NO:66), 17 (SEQ ID NO:67), 21 (SEQ ID NO:68), 25 (SEQ ID NO:69), 26 (SEQ ID NO:70), 27 (SEQ ID NO:71), 28 (SEQ ID NO:72), 30 (SEQ ID NO:73), 31 (SEQ ID NO:74), 33 (SEQ ID NO:75), 35 (SEQ ID NO:76), 36 (SEQ ID NO:77), 37 (SEQ ID NO:78), 38 (SEQ ID NO:79). For primer #186, Clone (SEQ ID NO) is as follows: 3 (SEQ ID NO:80), 5 (SEQ ID NO:81), 34 (SEQ ID NO:82).

Figure 2:
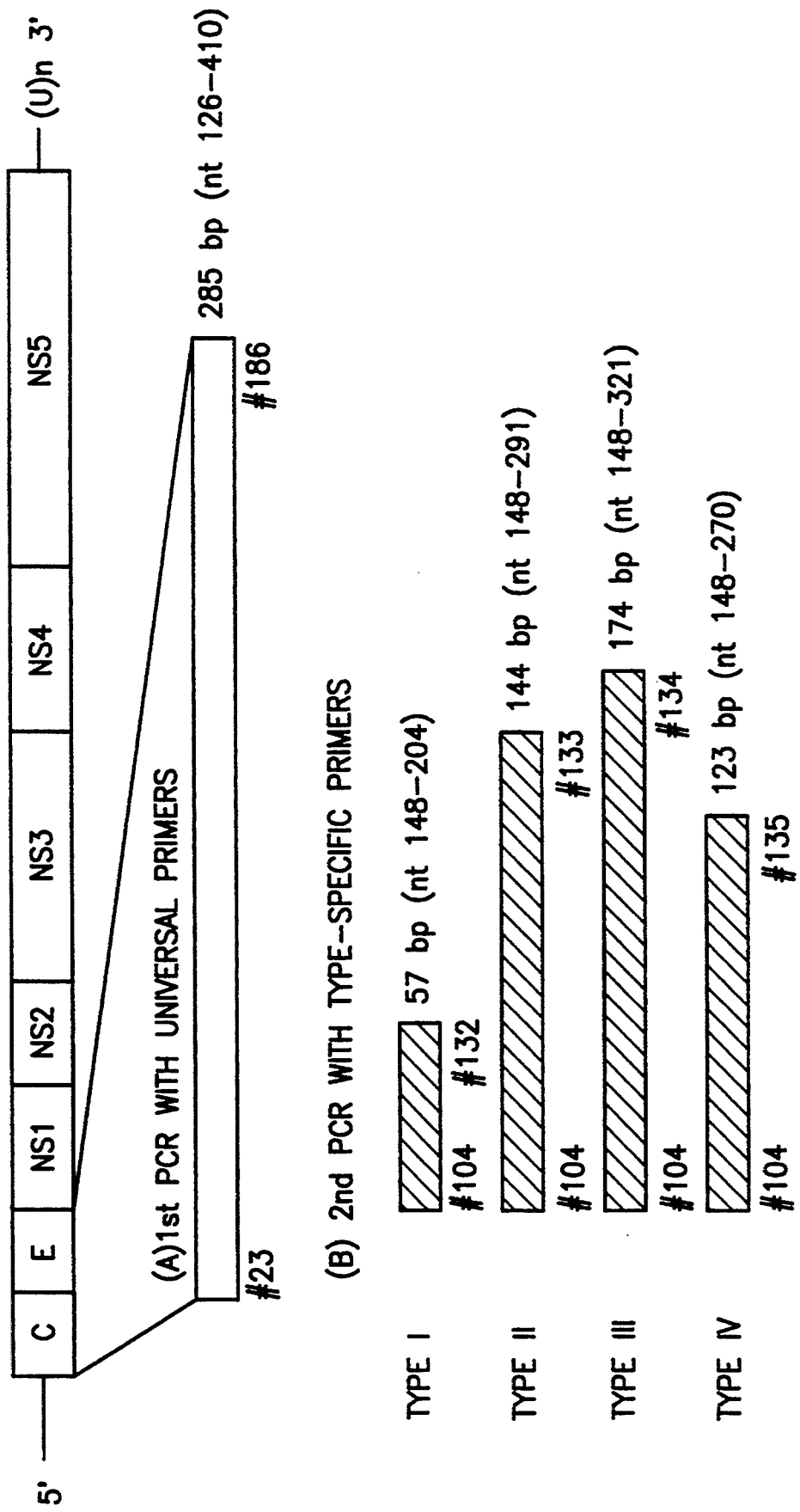

FIG. 2 is a diagram which shows the structure of the coding region of NANB hepatitis virus genome and PCR products using primers of the invention.

Figure 3:
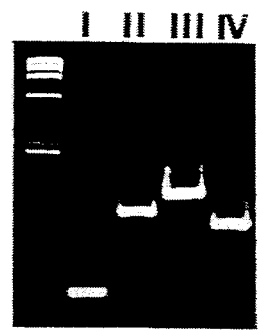

FIG. 3 is a photo which shows electrophoresis pattern of genotypes I to IV. Indicated on the left lane are migration positions of molecular size markers (φX174-RF DNA HaeIII digest; Pharmacia LKB).

Figure 4:
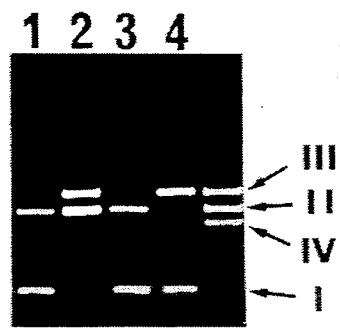

FIG. 4 is a photo which shows electrophoresis pattern of double infection cases. Migration positions of PCR products of the four different HCV types are indicated on the right.

Figure 5:

FIG. 5 is a photo which shows electrophoresis pattern of identification of infectious sources. Migration positions of PCR products of the four different HCV types are indicated on the right.

FIG. 6 is a table which shows nucleotide sequence of HCV in #256 (sequence list 7) and #296 (sequence list 9) region in 39 samples.

For primer #256, Clone (SEQ ID NO) is as follows: 1 (SEQ ID NO:83), 6 (SEQ ID NO:84), 25 (SEQ ID NO:85), 26 (SEQ ID NO:86), 29 (SEQ ID NO:87), 30 (SEQ ID NO:88). For primer #296, Clone (SEQ ID NO) is as follows: 5 (SEQ ID NO:89), 9 (SEQ ID NO:90), 14 (SEQ ID NO:91), 18 (SEQ ID NO:92), 24 (SEQ ID NO:93), 25 (SEQ ID NO:94), 28 (SEQ ID NO:95), 34 (SEQ ID NO:96), 35 (SEQ ID NO:97), 37 (SEQ ID NO:98), 39 (SEQ ID NO:99).

Figure 7:
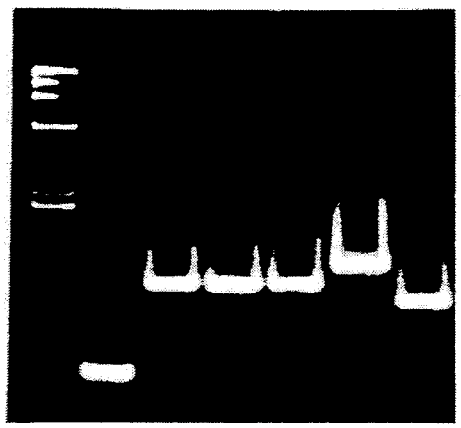

FIG. 7 is a photo which shows electrophoresis pattern of 6 HCV samples. Indicated on the left lane are migration positions of molecular size markers (φX174-RF DNA HaeIII digest; Pharmacia LKB).

Figure 8:
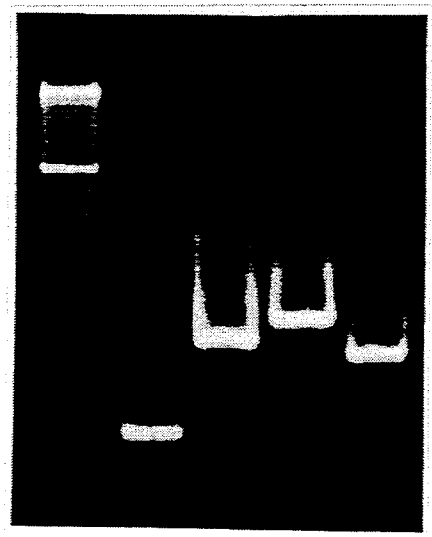

FIG. 8 is a photo which shows electrophoresis pattern of four HCV samples. Molecular markers in the left lane are 100 bp-ladder (Gibco, BRL).

In FIGS. 3–5, 7 and 8, I, II, III and IV show genotypes I, II, III and IV of HCV. 1, 2, 3, 4, 5 and 6 are lanes in electrophoresis pattern.

DETAILED DESCRIPTION OF THE INVENTION

In accordance with the present invention, there is provided a group of new oligonucleotides; in particular, new oligonucleotide primers #132 (sequence list 1), #133 (sequence list 2), #134 (sequence list 3), #135 (sequence list 4), #104 (sequence list 5), #23 (sequence list 6), #256 (sequence list 7), #186 (sequence list 8) and #296 (sequence list 9), which were obtained by chemical synthesis. These primers have the sequences shown in the attached sequence listing.

The novel oligonucleotides of the invention were determined as follows:

In a first step, HCV-cDNAs spanning the putative C gene were isolated from 39 serum or plasma samples from humans or chimpanzees, and nucleotide sequences of the cDNAs were determined as shown herein.

Four regions consisting of 20 successive nucleotides in common with all the cDNAs were selected at nt 148–167 (sequence list 5), nt 126–145 (sequence list 6), nt 139–158 (sequence list 7) and nt 391–410 (sequence list 8).

In the next step, regions were selected which consisted of 20 successive nucleotides which had high homology (basically containing less than 3 substitutions) in some cDNAs but showed low homology (basically containing more than 2 substitutions, and many substitutions observed in 5′ terminus) in other cDNAs at nt 185–204 (sequence list 1), nt 272–291 (sequence list 2), nt 302–321 (sequence list 3) and nt 251–270 (sequence list 4).

It was confirmed by the present invention that all the HCV-cDNAs could be classified into four groups when classified by the nucleotide sequence of five regions nt 185–204 (sequence list 1), nt 272–291 (sequence list 2), nt 302–321 (sequence list 3), nt 251–270 (sequence list 4) and nt 177–196 (sequence list 9) without an overlap.

Four nucleotides corresponding to regions having conservative sequences above were synthesized with Cyclone Plus DNA Synthesizer as #104 (sequence list 5) (nt 148–167), #23 (sequence list 6) (nt 126–145), #256 (sequence list 7) (nt 139–158) and #186 (sequence list 8) (nt 391–410). In the same manner, five nucleotides having complementary sequences to type-specific regions of HCV genomes above were synthesized as #132 (sequence list 1) (nt 185-204), #133 (sequence list 2) (nt 272-291), #134 (sequence list 3) (nt 302-321), #135 (sequence list 4) (nt 251-270) and #296 (sequence list 9) (nt 177-196).

The method of classification of HCV genotypes by amplifying cDNA using oligonucleotide primers #132, #133 (sequence list 2), #134 (sequence list 3), #135 (sequence list 4) and #296 (sequence list 9) having a complementary sequence to each region of HCV genomes as antisense primers, was completed.

Oligonucleotide primers #23 (sequence list 6) (nt 148-167), #104 (sequence list 5) (nt 126-145), #256 (sequence list 7) (nt 139-158) and #186 (sequence list 8) (nt 391-410) are well-conserved among different genotypes, and can be utilized as universal sense primers or antisense primers.

A preferred way to carry out the method of determining HCV genotypes is as follows: C-region cDNA is obtained by reverse transcription with primer #186 (sequence list 8), and the cDNA is amplified using oligonucleotide primer #23 (sequence list 8) or #256 (sequence list 7) as a sense primer and #186 (sequence list 8) as an antisense primer in the first stage PCR followed by amplification using #104 (sequence list 5) as a sense primer and #132 (sequence list 1), #133 (sequence list 2), #134 (sequence list 3) and #135 (sequence list 4) as antisense primers in the second stage PCR.

Since PCR products can be separated by electrophoresis and observed under u.v. light, the genotypes can be identified according to the length of the amplification products of the second stage PCR.

When previously isolated HCV genomes were classified by the method of the invention, they were divided into each one of four groups of type I, II, III and IV.

Names of genotypes were defined as follows; Type I: HCV group which can be amplified using antisense primer #132 (sequence list 1) and/or #296 (sequence list 9), and in the same manner, type II: #133 (sequence list 2), type III: #134 (sequence list 3) , and type IV: #135 (sequence list 4).

HCV clones HC-J1, HC-J4, HC-J5, HC-J6, HC-J7 and HC-J8, which were isolated by the inventors and disclosed in the above-identified Japanese patent applications, were classified into type I, II, III, III, IV and IV respectively using the method of determining HCV genotypes.

As shown in the Examples, 39 HCVcDNA clones obtained from serum or plasma of humans or chimpanzees were classified into each one of four genotypes I-IV. The homology of the nucleotide sequence of 39 samples were examined at the putative C gene nt 146-486. As a result, the homology was calculated as 95.1-97.5% among isolates classified into a genotype, while it was calculated as 77.9-91.0% among isolates classified into different genotypes. The results show that the method of the invention can identify HCV genotypes efficiently. (see Table 1; values represent mean ±S.D. percentage identity)

TABLE 1

Degree of sequence identity in a part of the putative C gene within and among four different types of HCV

| Number of isolates | Type | I | II | III | IV |
|---|---|---|---|---|---|
| 4 | I | 97.4 ± 0.3 | | | |
| 20 | II | 91.0 ± 1.0 | 95.3 ± 1.2 | | |
| 10 | III | 79.5 ± 0.8 | 79.4 ± 1.1 | 95.1 ± 1.0 | |
| 5 | IV | 79.1 ± 0.8 | 77.9 ± 0.7 | 85.5 ± 0.8 | 96.1 ± 0.6 |

In the specification, "nt" was numbered from the start of the single open reading frame, and "nc-nt" was numbered from putative 5' terminus of 5' non-coding region of the HCV genome.

Genotypes of Japanese sera from patients with HCV infection were examined by the method of the invention. As a result, as much as 82% were classified into type II, then 10%, 4% and 4% were respectively classified into type III, I and IV, among asymptomatic (healthy) carriers. In contrast, 60% were classified into type II, and 23% into type III among patients with chronic NANB liver disease. (Table 2) This result suggested that type III has higher possibility to cause an outbreak of chronic hepatitis than type II.

As described above, the method of the invention was shown to be useful in prevention and prediction of prognosis of HCV infection and type C chronic liver diseases.

TABLE 2

Prevalence of four HCV types in blood donors and patients with HCV infection

| Donor or patient | Sample number | Genotype | | | | Mixed |
| | | I | II | III | IV | |
|---|---|---|---|---|---|---|
| Blood donors | 159 | 6 (4%) | 131 (82%) | 16 (10%) | 6 (4%) | 0 |
| Acute hepatatis | 12 | 0 (0%) | 9 (75%) | 3 (25%) | 0 (0%) | 0 |
| Chronic hepatatis | 27 | 0 (0%) | 16 (59%) | 7 (26%) | 3 (11%) | 1 (I/II) |
| Liver cirrhosis | 24 | 2 (8%) | 15 (63%) | 5 (21%) | 2 (8%) | 0 |
| Hepatocellular carcinoma | 17 | 2 (11%) | 8 (47%) | 3 (18%) | 3 (18%) | 1 (II/III) |
| Hemophiliac | 11 | 3 (2%) | 3 (27%) | 2 (18%) | 1 (9%) | 2 (I/II, I/III) |

The method of the invention enables identification of HCV double infection and tracing of the source of infection.

In addition, as described in the Examples, significance was found in responses to interferon (hereinafter IFN) between types II and III among patients with chronic hepatitis C. This finding made it clear that the method to determine HCV genotypes of the invention is very useful in predicting the efficiency of drug therapy against hepatitis C.

The invention provides a method to definitely determine HCV genotypes, and it will be useful in many applications e.g. development of HCV IgG and vaccine, and establishment of the manner to administer them.

The invention provides a method to predict response of a patient with type C hepatitis to drug therapy.

The invention also provides oligonucleotides which can be utilized as sense primers or antisense primers in the method of determining HCV genotypes.

Examples of applications of this invention are shown below, however, the invention shall in no way be limited to those examples.

EXAMPLES

Example 1

Oligonucleotide #132 (sequence list 1), #133 (sequence list 2), #134 (sequence list 3), #135 (sequence list 4), #104 (sequence list 5), #23 (sequence list 6), #256 (sequence list 7), #186 (sequence list 8) and #296 (sequence list 9) were determined in the following way.

(1) Isolation of RNA

RNA of serum or plasma samples from Japanese blood donors testing positive for HCV antibody (c100-3 antibody; by Ortho HCV Ab ELISA, Ortho Diagnostic System, Tokyo), and that from the chimpanzee challenged with NANB hepatitis for infectivity and negative for HCV antibody, were isolated in the following method:

150 ml of each plasma sample was added to 150 ml of Tris chloride buffer (50 mM, pH 8.0, containing 150 ml NaCl, 10 mM EDTA) and centrifuged at $90 \times 10^3$ rpm for 15 minutes. The precipitate was suspended in Tris-chloride buffer (50 mM, pH 8.0, containing 200 mM NaCl, 10 mM EDTA, 2% (w/v) sodium dodecyl sulfate (SDS) and proteinase K 1 mg/ml), and incubated at 60° for 1 hour. Then the nucleic acids were extracted by phenol/chloroform and precipitated by ethanol to obtain RNAs.

(2) Detection of 5' Non-coding Region RNA and Core Region RNA by Polymerase Chain Reaction (PCR)

The isolated RNA were heated at 70° for 1 minute; using this as a template, cDNA was synthesized using oligonucleotide primer #36 (sequence list 10) (5' - A A C A C T A C T C G G C T A G C A G T - 3', nc–nt 246-265: antisense) and reverse transcriptase (Superscript, BRL, U.S.A.), and was provided to PCR as follows.

cDNA was amplified according to Saiki's method (Science (1988), volume 239, pages 487-491) using Gene Amp DNA Amplification Reagent (Perkin-Elmer Cetus) on a DNA Thermal Cycler (Perkin-Elmer Cetus). PCR was performed in two stages using 5' non-coding specific primer #32A (sequence list 11) (5' - C T G T G A G G A A C T A C T G T C T T - 3', nc–nt 45-64: sense) and #36 (sequence list 10) in the first stage; and #33 (sequence list 12) (5' - T T C A C G C A G A A A G C G T C T A G - 3', nc–nt 63-82: sense) and #48 (sequence list 13) (5' - G T T G A T C C A A G A A A G G A C C C - 3', nc–nt 188-207: antisense) locating inside of #32A (sequence list 11) and #36(sequence list 10), in the second stage.

28 samples obtained from sera of Japanese blood donors, 10 from patients with NANB liver disease, and one from chimpanzee observed to be infected with NANB hepatitis, all testing positive for 5' non-coding region RNA by said PCR in two stages, were provided to amplification of the C gene.

cDNA was synthesized for each sample using oligonucleotide #122 (sequence list 14) (5' - A G G T T C C C T G T T G C A T A A T T - 3', nt 487-506: antisense) as a primer, followed by generation of a product of 381 bp representing nt 126-506 corresponding to two third of C gene by PCR using #23 and #122.

PCR was carried out by the following reaction cycle: denaturation at 94° C. for 1 minute, annealing of primers at 55° C. for 1.5 minutes, and extension at 72° C. for 2 minutes. The products were cloned into the HincII site of M13mp19 phage vector. cDNA clones were sequenced in both directions by dideoxynucleotide chain termination method by the use of Sequenase version 2.0 (United States Biochemical, U.S.A.).

(3) Determination of Universal Primers and Type-specific Primers

Figure 1:
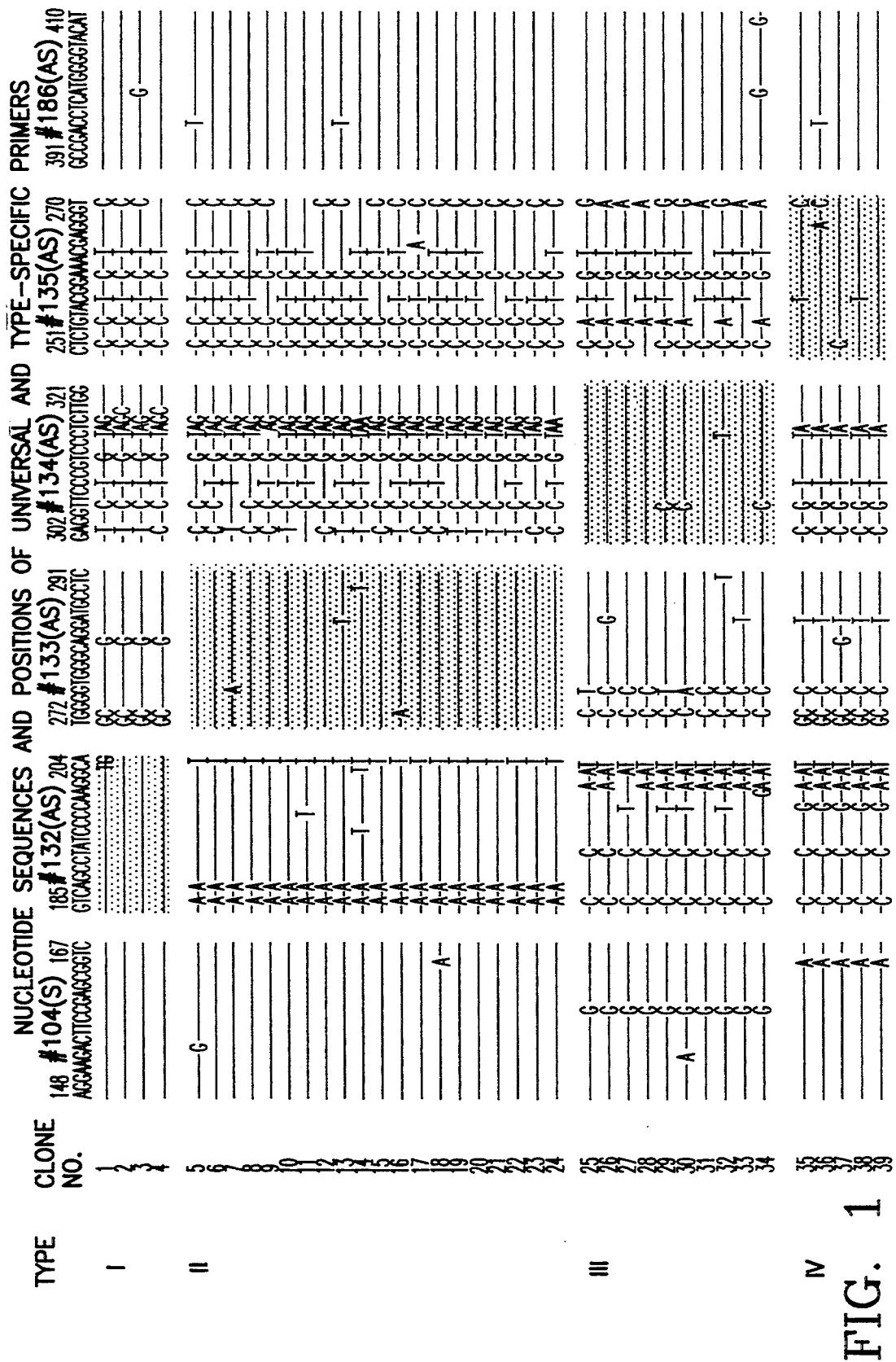
FIG. 1 is a table which shows the results of classification of genotypes and nucleotide sequences corresponding to primers on 39 samples.

In the nucleotide sequence of the obtained clones, some regions consisting of 20 successive nucleotides having conservative sequence (having substitution of less than 3 based in 20 bases) were selected. Nucleotide sequence in common with all the cDNAs were observed in regions nt 148-167 (sequence list 5), nt 126-145 (sequence list 6), nt 139-158 (sequence list 7) and nt 391-410 (sequence list 8). On the other hand, regions nt 177-196 (sequence list 9), nt 185-204 (sequence list 1), nt 272-291 (sequence list 2), nt 302-321 (sequence list 3) and nt 251-270 (sequence list 4) were recognized conservative in some isolates but not in common with others, which were thought to be genotype specific. (FIG. 1, FIG. 6).

Based on consensus sequence of each region, oligonucleotides #104 (sequence list 5, nt 148-167: sense), #23 (sequence list 6, nt 126-145: sense), #256 (sequence list 7, nt 139-158: sense) and #186 (sequence list 8, nt 391-410: antisense) were specified as universal primers.

In the same manner, oligonucleotides #132 (sequence list 1, nt 185-204: antisense), #133 (sequence list 2, nt 272-291: antisense), #134 (sequence list 3, nt 302-321: antisense), #135 (sequence list 4, nt 251-270: antisense) and #296 (sequence list 9, nt 177-196: antisense) were specified as type-specific primers.

Said oligonucleotides #104 (sequence list 5), #23 (sequence list 6), #256 (sequence list 7), #186 (sequence list 8), #132 (sequence list 1), #133 (sequence list 2), #134 (sequence list 3), #135 (sequence list 4) and #296 (sequence list 9) were synthesized with Cyclone Plus DNA Synthesizer (MilliGen/Biosearch, Division of Millipore) in the usual way.

Example 2—Genotype Determination System of the Invention (1) Typing of HCV-RNA Positive Samples Genotypes were determined using primers obtained in Example 1.

cDNAs were obtained using primer #186 (sequence list 8) from 39 sera used in Example 1. The reaction cycle was repeated 35 times with denaturation at 94° C. for 1 minute, primer annealing at 55° C. for 1.5 minutes, and primer extension at 72° C. for 2 minutes.

In the first stage PCR, 272 nucleotides of nt 139-410 were amplified with #256 (sequence list 7) and #186 (sequence list 8) for 35 cycles with a reaction cycle as described above.

A 1/50 amount of the products was subjected to second PCR for 30 cycles using a universal primer #104 (sequence list 5) and a mixture of equivalent amount of four type-specific primers, #132 (sequence list 1), #133 (sequence list 2), #134 (sequence list 3) and #135 (sequence list 4), with denaturation at 94° C. for 1 minute, primer annealing at 60° C. for 1 minute, and primer extension at 72° C. for 1.5 minutes. The products of the second PCR were subjected to electrophoresis on a composite agarose gel made from 1.5% NuSieve and 1.5% SeaKem (FMC BioProducts, U.S.A.), stained with ethidium bromide, and observed under u.v. light.

The products were identified by molecular sizes. That is, since a product amplified with #132 (sequence list 1) consists of 57 bp, and that with #133 (sequence list 2), #134 (sequence list 3) and #135 (sequence list 4) consist respectively of 144 bp, 174 bp and 123 bp, the position of a product shows its molecular size, and the primer used for amplification therefor. (FIG. 3).

Genotypes of 39 sera were completely identified as same result in Example I-(3) (FIG. 1), showing excellent specificity of type-specific primers of the invention.

Genotypes I, II, III and IV show types amplified with primer #132 (sequence list 1), #133 (sequence list 2), #134 (sequence list 3), and #135 (sequence list 4).

The same procedure with primer #23 (sequence list 6) in place of #256 (sequence list 7) in the first stage PCR gave the same result as (1) above.

(2) The same procedure with primer #23 (sequence list 6) in place of #104 (sequence list 5) in the second stage PCR gave same result as (1) above.

The same procedure with primer #256 (sequence list 7) in place of #104 (sequence list 5) in the second stage PCR gave the same result as (1) above.

(3) Variability of nucleotide sequence in nt 146–486 of C gene were examined on 39 sera classified into genotypes in (1) above. The clones classified into a genotype, which were amplified by one of the mixed antisense primers, showed homology as high as 95.1–97.5% while those classified into the other genotypes showed homology as low as 77.9–91.0%. (Table 1)

cDNAs of HC-J1, HC-J4, HC-J5, HC-J6 and HC-J7 or HCV isolates disclosed in previous Japanese applications were subjected to the method of determining genotypes using #132 (sequence list 1), 133 (sequence list 2), #134 (sequence list 3) and #135 (sequence list 4) as mixed antisense primers. As a result, HC-J1 was classified into type I, and HC-J4, HC-J5, HC-J6 and HC-J7 were respectively classified into types II, III, III and IV.

Example 3

Test sera from 96 patients, diagnosed histopathologically by biopsy as chronic hepatitis C and testing positive for HCV-RNA by PCR amplifying 5' non-coding gene, were subjected to classification of HCV genotypes in the same manner described in Example 2-(1). There was found 69 as type II (72%), 21 as type III (22%) and 6 as type IV (6%), where none was found as type I.

Drug therapy were carried out for said 96 patients with interferon α. Recombinant interferon-α2a (Roferon A, Nippon Roche, Tokyo) was administered subcutaneously 6 MU/day for seven successive days, followed by 3 MU/day for three days a week for 23 successive weeks.

Just after the 24-week IFN treatment, HCV-RNA was not found in 14 patients (20%) of type II, 14 (67%) of type III and 2 (33%) of type IV, from the result of PCR amplifying 5' non-coding gene. The HCV-RNA clearance rate of type II was found to be significantly higher than that of gene type III ($p<0.001$, Wilcoxon test). Moreover, type III showed very low HCV-RNA level after IFN treatment compared with types II and IV as shown in Table 3. For the level of HCV-RNA in Table 3, values of 1, 2, 3, etc. represent $10^0$, $10^1$, $10^2$, etc. CIU (Chimpanzee Infectious Unit)/ml.

TABLE 3

| HCV genotypes and response of chronic hepatitis C patients to interferon therapy. | | | | |
|---|---|---|---|---|
| Genotypes | Patients number | HCV-RNA quantity before IFN | HCV-RNA quantity after IFN | HCV-RNA eliminated cases |
| II | 69 | 5.2 ± 1.2 | 2.7 ± 2.0 | 14 (20.3%) |
| III | 21 | 4.7 ± 1.1 | 0.8 ± 1.3 | 14 (66.7%) |
| IV | 6 | 4.8 ± 1.6 | 3.3 ± 2.8 | 2 (33.3%) |
| Total | 96 | 5.1 ± 1.2 | 2.3 ± 2.1 | 30 (31.3%) |

As a result, some difference in response to interferon among genotypes was recognized among genotypes (which were classified by the method of determining genotypes). It became clear, therefore, that the invention is very useful in predicting the efficiency of drug therapy against hepatitis C. A study similar to that above can be conducted using other drugs or modalities of treatment. Differences in response of the four types of HCV to the treatment can thus be determined. Such data can then be used to predict the response to treatment of a patient infected with a strain of HCV. After the genotype of the patient's strain has been identified, the data from such a study will indicate the response to treatment of that strain which belongs to a particular type. For example, table 3 indicates that a patient infected with HCV type III would respond better to treatment with IFN than a patient infected with HCV type II.

Example 4

(1) HCV Genotyping of Japanese Cases

For the epidemiological study on HCV genotypes in Japan, samples were obtained from 159 blood donors, 80 patients with NANB liver disease and 11 hemophiliacs. HCV-RNAs were isolated from those sera, followed by cDNA synthesis and PCR to determine genotypes according to the procedure described in Example 2.

As the result, more than 80% of blood donors were typed as II as shown in Table 2. On the other hand, 48 of 80 patients with NANB liver diseases (60%) were typed as II, a significant difference ($p<0.01$) was recognized. Among those with hepatocellular carcinoma, only 48% were typed as II, while I (11%), III (18%), IV (18%) were found more often than among blood donors.

When blood donors and patients with NANB liver disease were compared on type III, 10% (16/159) were found in the former group, and 23% (18/80) in the latter group, a significant difference ($p<0.01$) was recognized. Significance was evaluated by Chi-squared analysis.

Five samples were typed as I and 4 as II among hemophiliacs, including cases of suspected double infection. The results suggested that some coagulation factor concentrates imported from the United States in the distant past, which had not been heat-inactivated, were possibly contaminated with HCV.

From the above, the method of the invention provides easy classification of HCV genotypes. In addition, the existence among genotypes of differences in the clinical course of hepatitis after infection with HCV suggests the usefulness of the method in the therapy and protection of NANB liver disease. As shown above, the results suggest that type III has higher possibility to cause an outbreak of chronic hepatitis than type II.

(b 2) Identification of Double Infection

Four cases of double infection were observed as shown in the electrophoresis pattern in FIG. 4. Two hemophiliacs (types I and II in lane 3; types I and III in lane 4) described in Example 3-(1), a patient with chronic hepatitis (types I and II in lane 1) and a patient with hepatoma (types II and III in lane 2) were included.

Double infection with HCV of different types in a case of a hemophiliac (lane 3) was confirmed by cloning of some cDNAs and sequence analysis within 341 bp in the C gene (nt 146–486); an identity of more than 99% was observed between isolates of clones assumed to be the same type, while only 88.8% between those assumed to be distinct types. In the same manner, cDNAs obtained from another hemophiliac (lane 4), a patient with chronic hepatitis and that with hepatocellular carcinoma were also classified into two types, where identities of 79.4%, 90.1% and 80.3% were respectively observed in distinct types. Those identities can be confirmed to show distinct types when compared with results in Example 2-(3)(Table 1).

Compared with conventional techniques to study genotypes, that is to isolate some clones from a sample, in order to determine those nucleotide sequences and then to calculate identities between sequences, the method of the invention provides an expeditious method of detection of double infection by HCV of distinct types.

(3) Identification of Infectious Source in Vertical and Horizontal Transmission

Test sera were obtained from 2 cases suspected of vertical (perinatal) transmission, and from a case of suspected horizontal transmission by needle stick exposure, and then subjected to determination of genotypes.

FIG. 5 shows the result of electrophoresis of PCR products following cDNA synthesis and PCR of typing according to the method described in Example 2. In FIG. 5, lane 1–4 were from two mother-to-baby pairs of perinatal transmission. Lane 1 and 2 were PCR products from a mother and baby of a family where genotypes of mother and baby were identified as type II; lanes 3 and 4 were from those of another family where genotypes of the mother and baby were identified as type III. Lane 5 and 6 were from a case of accidental HCV infection, where two genotypes from both donor (lane 5) and recipient (lane 6) were identical (type IV).

As the result, it became clear that the method of the invention is useful in tracing infectious sources of NANB hepatitis.

Example 5

HCV genomes HC-J2, HC-J3, (Japan J. Exp. Med. 60: 167–177, 1990) and HC-J8 (Japanese Patent Application No. 360441/91), which the inventors isolated and reported previously, were subjected to the determination of genotypes.

In the first stage PCR, #256 (sequence list 7) was used as a sense primer, and #186 (sequence list 8) as an antisense primer. In the second stage PCR, #104 (sequence list 5) was used as a sense primer, and mixed primer of #132 (sequence list 1), #133 (sequence list 2), #134 (sequence list 3) and #135 (sequence list 4) was used as antisense primer according to the method described in Example 2-(1). HC-J1, HC-J4 and HC-J6 described above were subjected to the test for comparison.

FIG. 7 shows the result of electrophoresis, where lanes 1–6 shows respectively HC-J1, HC-J2, HC-J3, HC-J4, HC-J6 and HC-J8. As the result, HC-J2 and HC-J3 were typed as II (the same as HC-J4), while HC-J8 was typed as IV.

In Examples above, primers were used selecting T for Y and G for R in #132 (sequence list 15); G for R, T for W and C for Y in #133 (sequence list 6); G for R in position five and A for R in position 16 in #134 (sequence list 17); A for R in positions one and 19, G for R in position 13 and C for Y in #135 (sequence list 18). With regard to universal primers, they were used selecting G for R in positions three, six, and 18, A for R in position seven and C for S in #104 (sequence list 19); A for M, T for N, G for R in position 15 and A for R in position 16 in #256 (sequence list 20); T for Y and G for R in #186 (sequence list 21).

The method of invention using primers selecting the other possible nucleotides gave same results as described above.

Example 6

Test sera No. 1, 2, 3 and 4, which were respectively typed as I, II, III and IV by the method described in Example 2-(1), were subjected to PCR for typing using equivalent mixture of primers #296 (sequence list 9), #133 (sequence list 2), #134 (sequence list 3) and #135 (sequence list 4) as antisense primer. cDNA priming and two stage PCR were carried out by the method described in Example 2-(1) except primer #296 (sequence list 9) was used for #132 (sequence list 1). PCR products were observed under u.v. light (after electrophoresis in composite agarose gel of 2% NuSieve and 2% SeaKem and stained with ethidium bromide). (FIG. 8)

As a result, the product generated by #296 (sequence list 9) (49 bp) was observed for sample No. 1 (lane 1), and products generated by #133 (sequence list 2), #134 (sequence list 3) and #135 (sequence list 4) were observed for sample No. 2-4. It became clear that the method of the invention using #296 (sequence list 9) instead of #132 (sequence list 1) gives the same result in determination of HCV genotypes.

The invention provides an expeditious method to classify HCV genomes into four types (genotypes).

The invention has many effects and applications, such as development of HC IgG and vaccine with high specificity and establishment of manner to administer them.

Moreover, the invention provides a method to identify HCV double infection and to track down the infectious source of HCV, and provides an excellent method in the study of HCV and in diagnosis, prevention and therapy of hepatitis C.

Further variations and modifications of the invention will become apparent to those skilled in the art from the foregoing and are intended to be encompassed by the claims appended hereto.

Japanese Patent Application No. 307296/91 filed on Sep. 9, 1991; 93960/92 filed on Feb. 28, 1992; and a Japanese Patent Application filed on Sep. 2, 1992, are all relied on and incorporated by reference; Hiroaki Okamoto and Tetsuo Nakamura are the inventors of all three Japanese applications.

Copending U.S. patent application Ser. No. 07/712,875 filed on Jun. 11, 1991 and 07/873,126 filed on Apr. 24, 1992, are incorporated by reference in their entirety.

Okamoto et al., "Typing hepatitis C virus by polymerase chain reaction with type-specific primers: application to clinical surveys and tracing infectious sources", *Journal of General Virology* (1992), volume 73, pages 673–679, is incorporated by reference in its entirety.

---

What is claimed:

1. Oligonucleotide #132 consisting of the nucleotide sequence of SEQ ID NO 1.

2. The oligonucleotide according to claim 1, wherein Y is T and R is G (SEQ ID NO 15).

3. Oligonucleotide #133 consisting of the nucleotide sequence of SEQ ID NO 2.

4. The oligonucleotide according to claim 3, wherein R is G, W is T, and Y is C (SEQ ID NO 16).

5. Oligonucleotide #134 consisting of the nucleotide sequence of SEQ ID NO 3.

6. The oligonucleotide according to claim 5, wherein the first occurrence of R is G and the second occurrence of R is A (SEQ ID NO 17).

7. Oligonucleotide #135 consisting of the nucleotide sequence of SEQ ID NO 4.

8. The oligonucleotide according to claim 7, wherein Y is C, the first occurrence of R is A, the second occurrence of R is G, and the third occurrence of R is A (SEQ ID NO 18).

9. Oligonucleotide #104 consisting of the nucleotide sequence of SEQ ID NO 5.

10. The oligonucleotide according to claim 9, wherein S is C; the first, second and fourth occurrences of R is G, and the third occurrence of R is A (SEQ ID NO 19).

11. Oligonucleotide #256 consisting of the nucleotide sequence of SEQ ID NO 7.

12. The oligonucleotide according to claim 11, wherein M is A, N is T, and the first occurrence of R is G and the second occurrence of R is A (SEQ ID NO 20).

13. Oligonucleotide #186 consisting of the nucleotide sequence of SEQ ID NO 8.

14. The oligonucleotide according to claim 13, wherein Y is T and R is G (SEQ ID NO 21).

15. Oligonucleotide #296 consisting of the nucleotide sequence of SEQ ID NO 9.

16. A method of determining the HCV genotype of a HCV strain, said method comprising subjecting said HCV strain to two stage PCR, wherein the first stage PCR comprises utilizing oligonucleotides #23 (SEQ ID NO 6) or #256 (SEQ ID NO 7) as sense primer and #186 (SEQ ID NO 8) as antisense primer and wherein the second stage PCR comprises utilizing a mixture of oligonucleotides #132 (SEQ ID NO 1), #133 (SEQ ID NO 2), #134 (SEQ ID NO 3), and #135 (SEQ ID NO 4) as antisense primers wherein oligonucleotide #296 (SEQ ID NO 9) may be substituted for oligonucleotide #132 (SEQ ID NO 1) and utilizing oligonucleotides #104 (SEQ ID NO 5) or #23 (SEQ ID NO 6) or #256 (SEQ. ID NO 7) as sense primer; said method further comprising comparing the product of said second stage PCR with HCV genotypes I, II, III and IV.

17. The method according to claim 16, further comprising measuring the molecular size of the resulting amplified cDNA.

18. A method to predict the response to drug therapy of a strain of HCV from a patient infected with said strain of HCV, said method comprising determining the sensitivity of HCV types I, II, III and IV to said drug therapy, determining the HCV genotype of said strain of HCV by the method according to claim 16, and in a final step comparing said HCV genotype of said strain prior to said drug therapy with said sensitivity of HCV types I, II, III and IV to said drug therapy.

* * * * *

UNITED STATES PATENT AND TRADEMARK OFFICE
CERTIFICATE OF CORRECTION

PATENT NO. : 5,427,909
DATED : Jun. 27, 1995
INVENTOR(S) : Hiroaki Okamoto

It is certified that error appears in the above-indentified patent and that said Letters Patent is hereby corrected as shown below:

On title page, item

[75] Please delete second inventor -- Tetsuo Nakamura--

[30] Please insert the third Japanese priority document
"276502/92    Japan    2September 1992"

Signed and Sealed this

Tenth Day of October, 1995

Attest:

BRUCE LEHMAN

Attesting Officer

Commissioner of Patents and Trademarks